United States Patent
Widenmeyer et al.

(10) Patent No.: US 9,964,514 B2
(45) Date of Patent: May 8, 2018

(54) METHOD FOR PRODUCING A GAS SENSOR DEVICE FOR DETECTING AT LEAST ONE GASEOUS ANALYTE, AND GAS SENSOR DEVICE FOR DETECTING AT LEAST ONE GASEOUS ANALYTE

(71) Applicant: Robert Bosch GmbH, Stuttgart (DE)

(72) Inventors: Markus Widenmeyer, Schoenaich (DE); Andreas Letsch, Stuttgart (DE); Denis Kunz, Untergruppenbach (DE); Robert Roelver, Calw-Stammheim (DE)

(73) Assignee: Robert Bosch GmbH, Stuttgart (DE)

( * ) Notice: Subject to any disclaimer, the term of this patent is extended or adjusted under 35 U.S.C. 154(b) by 0 days. days.

(21) Appl. No.: 15/527,601

(22) PCT Filed: Oct. 9, 2015

(86) PCT No.: PCT/EP2015/073463
§ 371 (c)(1),
(2) Date: May 17, 2017

(87) PCT Pub. No.: WO2016/087100
PCT Pub. Date: Jun. 9, 2016

(65) Prior Publication Data
US 2017/0322173 A1     Nov. 9, 2017

(30) Foreign Application Priority Data

Dec. 2, 2014     (DE) .................. 10 2014 224 587

(51) Int. Cl.
*G01N 27/407*     (2006.01)
*G01N 27/417*     (2006.01)
(Continued)

(52) U.S. Cl.
CPC ............. *G01N 27/407* (2013.01); *G01N 1/22* (2013.01); *G01N 27/18* (2013.01); *G01N 27/417* (2013.01);
(Continued)

(58) Field of Classification Search
CPC .... G01N 27/407; G01N 27/18; G01N 27/417; G01N 33/0027; G01N 27/4141; G01N 27/227; G01N 27/4045; G01N 2027/222
See application file for complete search history.

(56) References Cited

U.S. PATENT DOCUMENTS

| | | | |
|---|---|---|---|
| 2013/0075255 A1 | 3/2013 | Moon et al. | |
| 2014/0305812 A1* | 10/2014 | Fix | G01N 27/333 205/789 |
| 2014/0311905 A1* | 10/2014 | Stetter | B01J 31/06 204/424 |

FOREIGN PATENT DOCUMENTS

| | | |
|---|---|---|
| DE | 10 2013 204 665 A1 | 9/2014 |
| DE | 10 2013 204 197 A1 | 10/2014 |
| DE | 10 2013 208 939 A1 | 11/2014 |

OTHER PUBLICATIONS

International Search Report corresponding to PCT Application No. PCT/EP2015/073463, dated Dec. 11, 2015 (German and English language document) (7 pages).

* cited by examiner

*Primary Examiner* — Kabir A Timory
(74) *Attorney, Agent, or Firm* — Maginot, Moore & Beck LLP

(57) ABSTRACT

A method for producing a gas sensor device for detecting a gaseous analyte includes providing a sensor body comprising a semiconductor substrate, in which a cavity section is shaped, and a solid electrolyte layer arranged at a surface of the substrate. The electrolyte layer is not covered by the (Continued)

substrate in the cavity section. The method includes producing a signal conductor layer deposited dry-chemically at a substrate side of the sensor body, such that, in the region of the electrolyte layer not covered by the substrate in the cavity section, a cutout section is shaped in the signal conductor layer, in which the signal conductor layer is removed or not deposited. The method includes applying measuring electrodes to the electrolyte layer by a wet-chemical process. One measuring electrode is arranged in the cutout section and one measuring electrode is arranged on an electrolyte layer side of the sensor body.

10 Claims, 13 Drawing Sheets

(51) Int. Cl.
    *G01N 27/18*     (2006.01)
    *G01N 1/22*     (2006.01)
    *G01N 33/00*     (2006.01)

(52) U.S. Cl.
    CPC ..... *G01N 27/4175* (2013.01); *G01N 33/0027* (2013.01)

METHOD FOR PRODUCING A GAS SENSOR DEVICE FOR DETECTING AT LEAST ONE GASEOUS ANALYTE, AND GAS SENSOR DEVICE FOR DETECTING AT LEAST ONE GASEOUS ANALYTE

This application is a 35 U.S.C. § 371 National Stage Application of PCT/EP2015/073463, filed on Oct. 9, 2015, which claims the benefit of priority to Serial No. DE 10 2014 224 587.7, filed on Dec. 2, 2014 in Germany, the disclosures of which are incorporated herein by reference in their entireties.

BACKGROUND

The present disclosure relates to a method for producing a gas sensor device for detecting at least one gaseous analyte, to a gas sensor device for detecting at least one gaseous analyte, to a corresponding device and also to a corresponding computer program.

By way of example, miniaturized solid electrolyte gas sensors which can be manufactured using micromechanical methods and processes can be used in particular for measuring a residual oxygen proportion in the exhaust gas flow of internal combustion engines or for so-called lambda measurement or the like.

SUMMARY

Against this background, the approach presented here presents a method for producing a gas sensor device for detecting at least one gaseous analyte, a gas sensor device for detecting at least one gaseous analyte, furthermore a device which uses this method, and finally a corresponding computer program. Advantageous configurations are evident from the following description.

In accordance with embodiments of the present disclosure, a solid-electrolyte-based microelectrochemical sensor (MECS) or a miniaturized solid electrolyte gas sensor can be provided in which, in particular even in the case of extreme surface topographies, for example with deep cavities, a combination of wet-chemically deposited, functional sensor electrodes and dry-chemically deposited electrodes for electrically forwarding the sensor signal can be realized. The method can also be implemented in an adapted manner in other applications or for producing other devices, in order to produce structured layers on greatly topographically shaped surfaces or wet-chemically applied metal electrodes on a topographically demanding surface.

Advantageously, in accordance with embodiments of the present disclosure, firstly it is possible to enable, even on topographically demanding surfaces, originally closed layers or films to be locally and selectively structured or layer material to be removed in a targeted manner, in order thus for example to combine wet-chemically deposited, functional sensor electrodes and dry-chemically deposited electrodes for electrically forwarding the sensor signal. In this case, it is possible to use in particular a laser ablation for selectively stripping films on depth-structured surfaces. Moreover, advantageously, in accordance with embodiments of the present disclosure, secondly it is possible to enable wet-chemical electrodes to be used in a depression, such as, for example, a cavity in an MECS sensor element, and an electrical electrode contact by means of a compact film applied dry-chemically to be led out of the cavity onto a rear side of the sensor. In this case, in particular, a directional deposition method can be used in which shading effects can have the consequence that, for example, only sidewalls of a cavity are coated, but a bottom of a cavity is not coated.

It is possible, in particular, to enable new fields of application to be opened up for MEMS technology (MEMS=microelectromechanical systems), such as, for example, by means of the abovementioned combination of dry-chemically and wet-chemically produced layers for miniaturized solid electrolyte gas sensors or MECS sensor elements which can be fabricated using micromechanical methods and processes. Such sensor elements can be used for example for measuring a residual oxygen proportion or for so-called lambda measurement in exhaust gases of internal combustion engines.

One possible sensor concept for such a gas sensor can comprise a use of a self-supporting or partially exposed solid electrolyte membrane, wherein in one variant an exposure can be effected by etching back a semiconductor substrate or silicon wafer in the membrane region. In this case, a depth of a cavity shaped in this way can correspond to a thickness of a wafer or substrate material. The self-supporting membrane or an exposed section of the solid electrolyte layer is coated on both sides with exhaust-gas-resistant and thermally stable, porous electrodes or measuring electrodes, such as can be shaped for example from platinum or some other metal. One variant in order to be able to produce for example functional, porous platinum electrodes as measuring electrodes can comprise a wet-chemical coating of functionalized platinum nanoparticles from a liquid solution. By drying and sintering initially liquid coating material, it is possible to produce a compact layer of sintered platinum particles which is resistant in particular to thermal stress and ingress of moisture.

In order to be able to prevent a situation in which, in the case of a whole-area wet-chemical coating at a semiconductor substrate, for example on a sensor rear side, on cavity inner sides and at edges a spalling of the coating and film cracks occur, in accordance with embodiments of the present disclosure for a continuous, electrically conductive contacting from an electrolyte rear side onto a wafer rear side it is possible to dispense with in particular a wet-chemical application of continuous or whole-area electrode films. Therefore, dry-chemically applied electrodes can be used for signal conduction or for electrical connection of the measuring electrodes since wet-chemically applied electrodes for this purpose have anyway a lower specific conductivity than for example sputtered, relatively pore-free metal layers, which would make it more difficult to transmit a voltage signal over a relatively long distance, such as, for example, from the solid electrolyte layer as far as a sensor plug contact or the like. This can be remedied by a combination of a dry-chemical deposition method, such as, for example, sputtering or electron beam evaporation, on a side of the semiconductor substrate facing away from the solid electrolyte layer or on a wafer rear side and cavity walls and a wet-chemical deposition of a porous measuring electrode layer, for example composed of platinum, on an electrolyte surface at the bottom of the cavity. For this purpose, for a realization of such a combination of two coating methods, it is possible to arrange a dry-chemically deposited, for example sputtered, closed and gas-tight signal conductor layer composed of platinum or the like in a manner restricted to cavity walls and wafer rear side.

Whereas in standard MEMS fabrication, lithography processes can normally be used to fulfill such a requirement, in which lithography processes a photosensitive resist applied over the whole area can be locally structured by means of lithography masks and a structure transfer can subsequently be effected by means of etching processes or a lift-off process, in accordance with embodiments of the present disclosure it is possible to achieve in particular a local structuring even in the case of extreme topographies or it is possible to enable a locally delimited layer deposition or structure definition even on extremely shaped surface topographies. Consequently, it is possible to realize the combination of dry-chemically and wet-chemically produced layers or films even on extreme surface topographies, such as, for example, when deep cavities are present, which, by means of photolithography, for example, would range from more complex to impossible or unsatisfactory. Unlike in the case of photolithography, therefore, in particular even on greatly topographically shaped surfaces, in accordance with embodiments of the present disclosure it is possible to prevent the occurrence of a structure loss at deep locations on account of diffuse light scattering as a result of an increased distance between lithography mask and photoresist, a resist separation at structure edges when applying resist to a wafer surface or the like.

A method for producing a gas sensor device for detecting at least one gaseous analyte is presented, wherein the method comprises the following steps:

providing a sensor main body comprising a semiconductor substrate, in which at least one cavity section is shaped, and a solid electrolyte layer arranged at a first main surface of the semiconductor substrate, wherein the solid electrolyte layer is left free of the semiconductor substrate in the at least one cavity section;

producing a signal conductor layer deposited dry-chemically at a semiconductor substrate side of the sensor main body, such that, in the region of the solid electrolyte layer not covered by the semiconductor substrate in the at least one cavity section, at least one cutout section is shaped in the signal conductor layer, in which the signal conductor layer is cut out; and applying at least two measuring electrodes to the solid electrolyte layer by means of a wet-chemical process, wherein a first measuring electrode is arranged in the at least one cutout section of the signal conductor layer and a second measuring electrode is arranged on a solid electrolyte layer side of the sensor main body.

In the present case, a cut-out section of a layer can be understood to mean for example an opening in the relevant layer. In this case, the opening can also be partly filled again, but be completely enclosed by material of the relevant layer.

The gas sensor device can be designed to detect the at least one gaseous analyte qualitatively and additionally or alternatively quantitatively. The at least one gaseous analyte can comprise for example oxygen and additionally or alternatively nitrogen oxides. In this case, the gas sensor device can be used for example for an exhaust gas sensor system in motor vehicles, for an exhaust gas sensor system in stationary heating installations, for example, for fire alarm systems, for a gas sensor system in mobile electronic appliances, such as, for example, cellular phones, for a respiratory gas analysis, for an industrial process monitoring, etc. In particular, the gas sensor device can for example be used in motor vehicles and be designed to monitor or to regulate exhaust gas aftertreatment systems. The semiconductor substrate can be shaped from at least one of a plurality of materials which can be processed by means of processes from the field of semiconductor processing. The solid electrolyte layer can comprise an ion-conducting, for example ceramic, material, in particular an oxygen-ion-conducting ceramic material.

In accordance with one embodiment, in the step of producing, the signal conductor layer is deposited dry-chemically and is removed by means of selective laser ablation in the at least one cutout section. In this case, the signal conductor layer and the solid electrolyte layer can have different optical properties and additionally or alternatively mechanical properties, such as, for example, optical absorption, strength, thermal expansion or the like. When implementing the laser ablation, a laser beam profile can be adaptively adapted to a structure height of the semiconductor substrate and of the at least one cavity section. Such an embodiment affords the advantage that the at least one cutout section can be shaped in a precise manner in the signal conductor layer. Moreover, even across pronounced surface topographies, it is possible to obtain a uniform degree of ablation or stripping independently of a structure height.

In this case, the selective laser ablation can be performed from the semiconductor substrate side of the sensor main body. Additionally or alternatively, the laser ablation can be performed from the solid electrolyte layer side of the sensor main body through the solid electrolyte layer. In this case, the solid electrolyte layer can be transparent to laser light used during the laser ablation. Such an embodiment affords the advantage that a flexibility in a process configuration or method configuration can be increased and, if appropriate, a production of the sensor device can thus be facilitated.

In accordance with one embodiment, in the step of producing, the signal conductor layer can be deposited dry-chemically in a defined deposition direction. In this case, depending on the deposition direction and a geometry of the at least one cavity section, the at least one cutout section can be shaded from a material of the signal conductor layer. In this case, at least the solid electrolyte layer exposed in the cavity section of the semiconductor substrate can be arranged depending on the deposition direction relative to a reference plane of the sensor main body or depending on an orientation of the sensor main body in relation to a deposition source in a flow shadow of the directionally deposited material of the signal conductor layer. Such an embodiment affords the advantage that the signal conductor layer with the at least one cutout section can be produced by means of a particularly simple process in for example only one step.

Moreover, in the step of providing, a sensor main body can be provided, in the semiconductor substrate of which the at least one cavity section is shaped with a depth of more than 100 micrometers or more than 200 micrometers.

Furthermore, the method can comprise a step of coating the semiconductor substrate with a passivation layer. In this case, the step of coating can be carried out before the step of producing the signal conductor layer. The signal conductor layer can thus be produced at least over a partial area on the passivation layer. Such an embodiment affords the advantage that it is possible to avoid a degradation of a surface of the semiconductor substrate during operation of the sensor device, in particular during use in the exhaust gas of internal combustion engines.

Moreover, in the step of producing, the signal conductor layer can be deposited dry-chemically and be covered with a masking layer. In this case, the masking layer can be removed by means of selective laser ablation locally in at least one cutout section and the signal conductor layer can be removed in the latter or, if required, in a plurality of the cutout sections produced. Moreover, the masking layer can be eliminated. Consequently, the step of producing can comprise a substep of depositing, a substep of covering, a substep of ablating removal and a substep of removing and also an optional substep of eliminating. In this case, the substeps can be performed in the order mentioned above. Such an embodiment affords the advantage that the signal conductor layer with the at least one cutout section can be produced even in cases in which direct ablation or erosion of the signal conductor layer would be difficult or impossible.

Furthermore, a gas sensor device for detecting at least one gaseous analyte is presented, wherein the gas sensor device comprises the following features:

a sensor main body comprising a semiconductor substrate, in which at least one cavity section is shaped, and a solid electrolyte layer arranged at a first main surface of the semiconductor substrate, wherein the solid electrolyte layer is left free of the semiconductor substrate in the at least one cavity section;

a signal conductor layer deposited dry-chemically at a semiconductor substrate side of the sensor main body, wherein in the region of the solid electrolyte layer not covered by the semiconductor substrate in the at least one cavity section, at least one cutout section is shaped in the signal conductor layer, in which the signal conductor layer is cut out; and at least two measuring electrodes applied to the solid electrolyte layer by means of a wet-chemical process, wherein a first measuring electrode is arranged in the at least one cutout section of the signal conductor layer and a second measuring electrode is arranged on a solid electrolyte layer side of the sensor main body.

The gas sensor device may have been or be produced by implementation of an embodiment of the method mentioned above.

The approach presented here furthermore provides a device designed to carry out, activate or implement the steps of a variant of a method presented here in corresponding apparatuses. This embodiment variant of the disclosure in the form of a device also enables the object on which the disclosure is based to be achieved rapidly and efficiently.

In the present case, a device can be understood to mean an electrical appliance which processes sensor signals and outputs control and/or data signals in a manner dependent thereon. The device can have an interface which can be designed in terms of hardware and/or software. In the case of a design in terms of hardware, the interfaces can be for example part of a so-called system ASIC that includes a wide variety of functions of the device. However, it is also possible for the interfaces to be dedicated integrated circuits or to consist at least partly of discrete components. In the case of a design in terms of software, the interfaces can be software modules present for example on a microcontroller alongside other software modules.

Also of advantage is a computer program product or computer program comprising program code which can be stored on a machine-readable carrier or storage medium such as a semiconductor memory, a hard disk storage unit or an optical storage unit and is used for carrying out, implementing and/or activating the steps of the method according to one of the embodiments described above, particularly if the program product or program is executed on a computer or a device.

In accordance with embodiments of the present disclosure, an embodiment of the gas sensor device mentioned above can be used in microsystems engineering as a platform or basic building block in order to integrate further sensor functions, such as, for example, pressure detection, particle detection, lambda sensor system, hydrocarbon detection, etc., on a single chip and to evaluate them in a combined manner.

BRIEF DESCRIPTION OF THE DRAWINGS

The approach presented here is explained in greater detail below by way of example with reference to the accompanying drawings, in which.

DETAILED DESCRIPTION

In the following description of expedient exemplary embodiments of the present disclosure, identical or similar reference signs are used for the similarly acting elements illustrated in the different figures, a repeated description of these elements being dispensed with.

Figure 1:
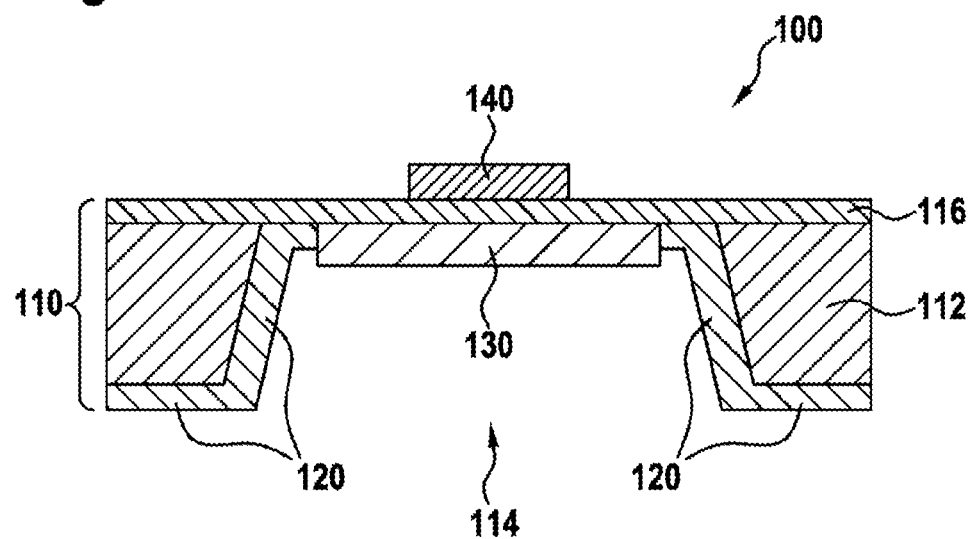
FIG. 1 shows a schematic sectional illustration of a gas sensor device in accordance with one exemplary embodiment of the present disclosure.

FIG. 1 shows a schematic sectional illustration of a gas sensor device 100 in accordance with one exemplary embodiment of the present disclosure. The gas sensor device 100 is designed for detecting at least one gaseous analyte. The at least one gaseous analyte here is oxygen, for example. The gas sensor device 100 is embodied as a microelectrochemical sensor or gas sensor, in particular oxygen sensor. In this case, the gas sensor device 100 is usable for example for a gas sensor system or exhaust gas sensor system in motor vehicles, stationary heating installations, fire alarm systems, mobile electronic appliances, such as, for example, cellular phones, respiratory gas analyzers, for an industrial process monitoring process, etc.

The gas sensor device 100 comprises a sensor main body 110. The sensor main body 110 comprises a semiconductor substrate 112. The semiconductor substrate 112 comprises silicon, for example, as substrate material. However, the semiconductor substrate 112 has a first main surface and an opposite, second main surface. In accordance with the exemplary embodiment of the present disclosure illustrated in FIG. 1, by way of example, only one cavity section 114 or recess section is shaped in the semiconductor substrate 112. In this case, the cavity section 114 extends as a through opening through the semiconductor substrate 112 from the second main surface as far as the first main surface of the semiconductor substrate 112. The cavity section 114 has a trapezoidal sectional profile, for example. In this case, the sectional profile of the cavity section 114 tapers from the second main surface toward the first main surface of the semiconductor substrate 112. The sensor main body 110 furthermore comprises a solid electrolyte layer 116. The solid electrolyte layer 116 is arranged at the first main surface of the semiconductor substrate 112. In the cavity section 114, the solid electrolyte layer 116 is not covered by the semiconductor substrate 112. Consequently, the sensor main body 110 comprises the semiconductor substrate 112 with the cavity section 114 and the solid electrolyte layer 116. The sensor main body 110 therefore has a solid electrolyte layer side and a semiconductor substrate side.

The gas sensor device 100 also comprises a signal conductor layer 120. The signal conductor layer 120 is applied to the semiconductor substrate side of the sensor main body 110 by means of dry-chemical deposition. The signal conductor layer 120 is shaped on an electrically conductive material. In accordance with the exemplary embodiment of the present disclosure as illustrated in FIG. 1, the signal conductor layer 120 on the semiconductor substrate side of the sensor main body 110 covers a surface of the semiconductor substrate 112 and a partial section of the solid electrolyte layer 116 in the cavity section 114. To put it another way, in this case the signal conductor layer 120 covers the second main surface of the semiconductor substrate 112, sidewalls of the cavity section 114 and the partial section of the solid electrolyte layer 116 in the cavity section 114. The signal conductor layer 120 has a cutout section in the region of the solid electrolyte layer 116 not covered by the semiconductor substrate 112 in the cavity section 114, in which cutout section the signal conductor layer 120 is removed or not deposited (that is to say cut out).

In accordance with the exemplary embodiment of the present disclosure as illustrated in FIG. 1, the gas sensor device 100 further comprises by way of example only two measuring electrodes 130 and 140. The two measuring electrodes 130 and 140 are applied to the solid electrolyte layer 116. In this case, the two measuring electrodes 130 and 140 are applied to the solid electrolyte layer 116 by means of a wet-chemical process. A first measuring electrode 130 is arranged in the cutout section of the signal conductor layer 120. A second measuring electrode 140 is arranged on a solid electrolyte layer side of the sensor main body 110. The measuring electrodes 130 and 140 are designed for an electrochemical interaction with the at least one gaseous analyte. In the cutout section, the signal conductor layer 120 is interrupted by the first measuring electrode 130. The first measuring electrode 130 is electrically conductively contacted by means of the signal conductor layer 120. In the sectional illustration in FIG. 1, the first measuring electrode 130 in this case has two interfaces with the signal conductor layer 120.

In accordance with one exemplary embodiment, the signal conductor layer 120 can cover a smaller proportion of the semiconductor substrate 112 and/or of the solid electrolyte layer 116 in the cavity section 114 and optionally have a smaller interface with the first measuring electrode 130 than in the case of the exemplary embodiment illustrated in FIG. 1.

FIGS. 2A to 2G show schematic sectional illustrations of at least partial sections of a gas sensor device in accordance with an exemplary embodiment of the present disclosure in different production states in the implementation of a variant of a production method. The gas sensor device is for example the gas sensor device from FIG. 1.

Figure 2A:
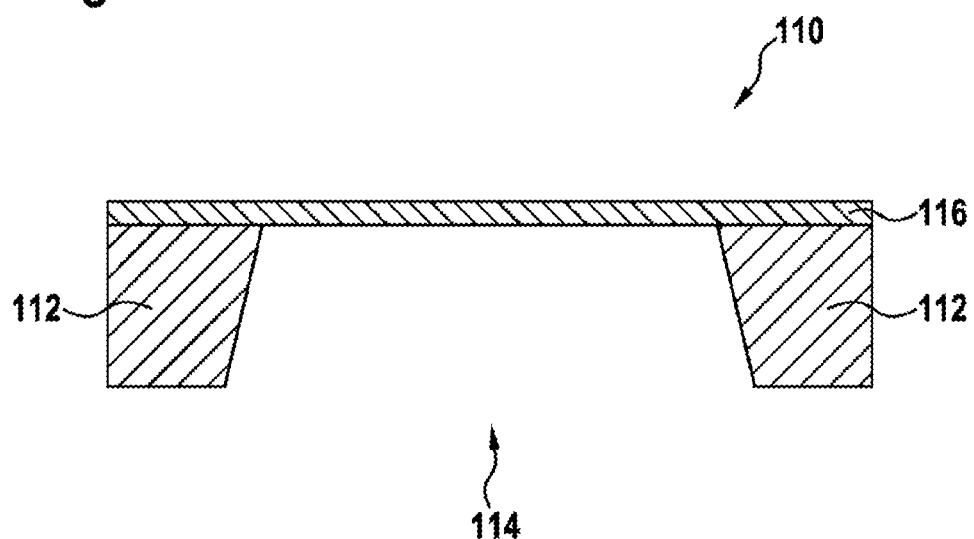
FIGS. 2A to 6B show schematic sectional illustrations of gas sensor devices in accordance with exemplary embodiments of the present disclosure in different production states.

In this case, FIG. 2A shows a schematic sectional illustration of a sensor main body 110 of the gas sensor device. In this case, the sensor main body 110 is shown after a step of providing the sensor main body 110 in the production method. The sensor main body 110 comprises the semiconductor substrate 112 with the cavity section 114 and the solid electrolyte layer 116. The solid electrolyte layer 116 is embodied for example as a partially exposed or self-supporting yttrium-stabilized zirconium oxide electrolyte membrane or YSZ electrolyte membrane.

Figure 2B:
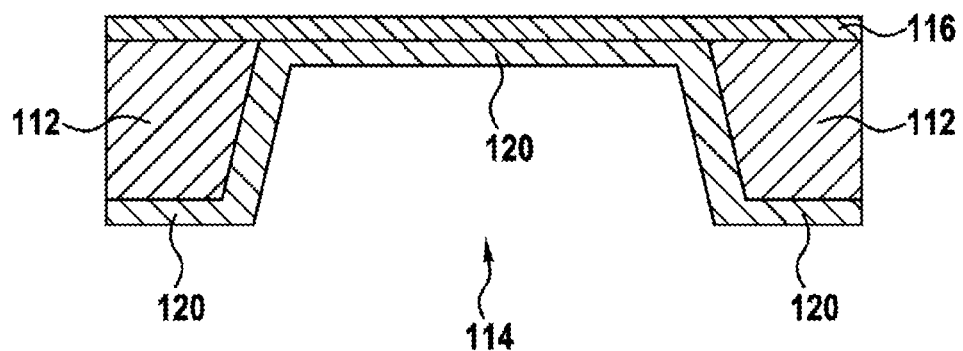

FIG. 2B shows a schematic sectional illustration of the sensor main body from FIG. 2A with a deposited signal conductor layer 120. Thus, in this case the sensor main body is shown in a production state in which the signal conductor layer 120 is produced by means of dry-chemical deposition, in particular by means of dry-chemical platinum coating, on the semiconductor substrate side of the sensor main body. In this case, the signal conductor layer 120 is deposited over the whole area on the semiconductor substrate side of the sensor main body.

Figure 2C:
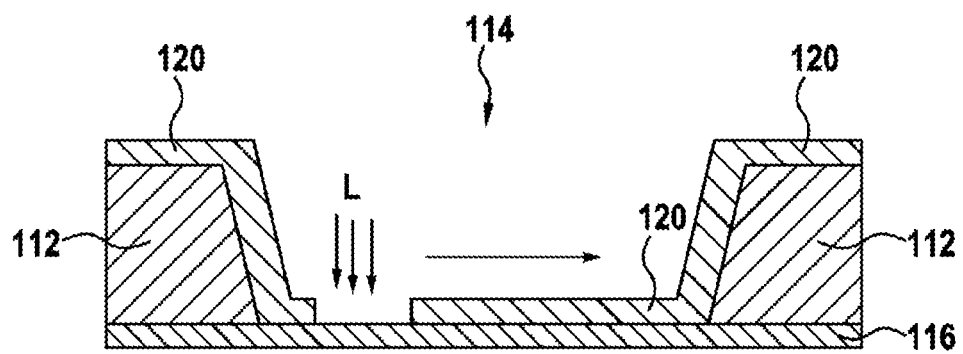

FIG. 2C shows a schematic sectional illustration of the sensor main body with the signal conductor layer 120 from FIG. 2B during the progression of a laser ablation in the context of the production method. By means of a laser L, a partial section—adjoining the solid electrolyte layer 116—of the signal conductor layer 120 in the cavity section 114 is removed by laser ablation. In this case, the laser L is arranged on the part of the cavity section 114. A local laser ablation is thus effected in the cavity section 114 or at the bottom of the cavity. In FIG. 2C, a direction of movement of the laser L is illustrated symbolically by an arrow.

Figure 2D:
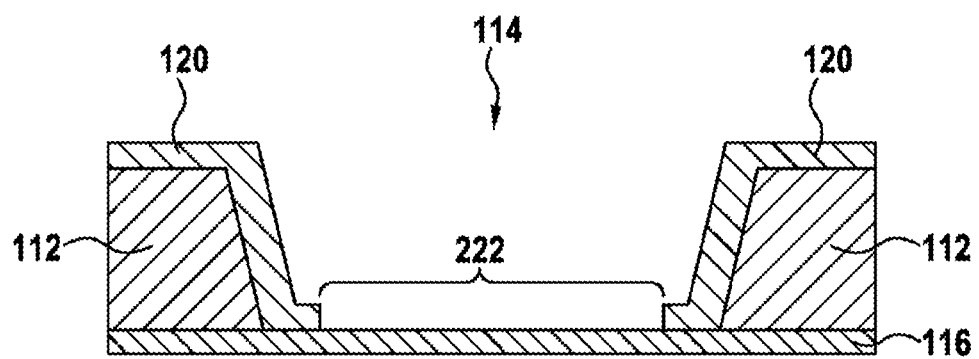

FIG. 2D shows a schematic sectional illustration of the sensor main body with the signal conductor layer 120 from FIG. 2C after the laser ablation. In this case, the partial section—adjoining the solid electrolyte layer 116—of the signal conductor layer 120 in the cavity section 114 has been removed by laser ablation. Consequently, the cutout section 222 mentioned in FIG. 1 has been produced in the signal conductor layer 120. A material of the signal conductor layer 120 has been removed in the cutout section 222. To put it another way, the signal conductor layer 120 is interrupted in the cutout section 222. The gas sensor device is thus shown in a partly fabricated state in FIG. 2D.

During such a selective ablation of platinum on YSZ by means of a laser L, the platinum of the signal conductor layer 120 is removed in the cutout section 222 for example locally by individual laser pulses. A planar ablation can be realized in particular by the laser pulses being positioned directly alongside one another with a certain overlap. In order to make a laser focus adaptable to an altered structure height during the ablation, either height information is storable in a laser ablation program which is programmable in a laser device, or an adaptive focus system is usable which adapts the laser focus to the actual structure height by means of an autofocus system before ablation pulses are emitted. Beam shaping with the aid of an axicon is likewise realizable, wherein a high depth of focus is achievable both for a robust process and for a production of small structure sizes.

Figure 2E:
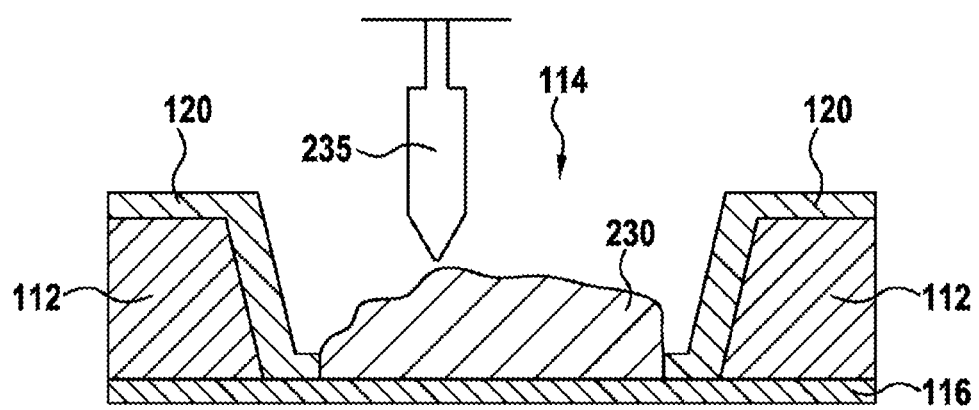

FIG. 2E shows a schematic sectional illustration of the partly fabricated gas sensor device from FIG. 2D with an applied electrode material 230 for a measuring electrode. In this case, the electrode material 230 is applied to the solid electrolyte layer 116 in the cutout section. To put it precisely, the electrode material 230 is applied to the solid electrolyte layer 116 wet-chemically in the cutout section of the signal conductor layer 120. The electrode material 230 is for example a platinum-containing material, in particular a platinum nanoparticle solution. The wet-chemical application of the electrode material 230 is carried out in this case for example by dispensing by means of an application tool 235.

Figure 2F:
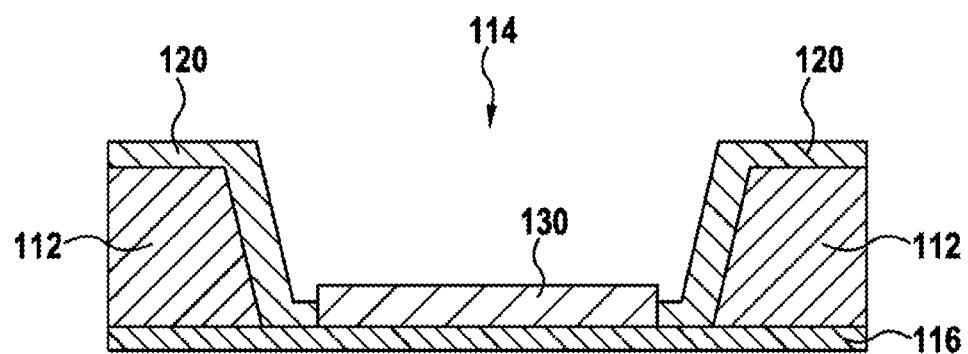

FIG. 2F shows a schematic sectional illustration of the partly fabricated gas sensor device from FIG. 2E with sintered electrode material or produced first measuring electrode 130. FIG. 2F thus illustrates the partly fabricated gas sensor device in a state in which the electrode material from FIG. 2E has been solidified by sintering and the first measuring electrode 130 has thus been produced. The first measuring electrode 130 is arranged on the solid electrolyte layer 116 in the cutout section of the signal conductor layer 120.

Figure 2G:
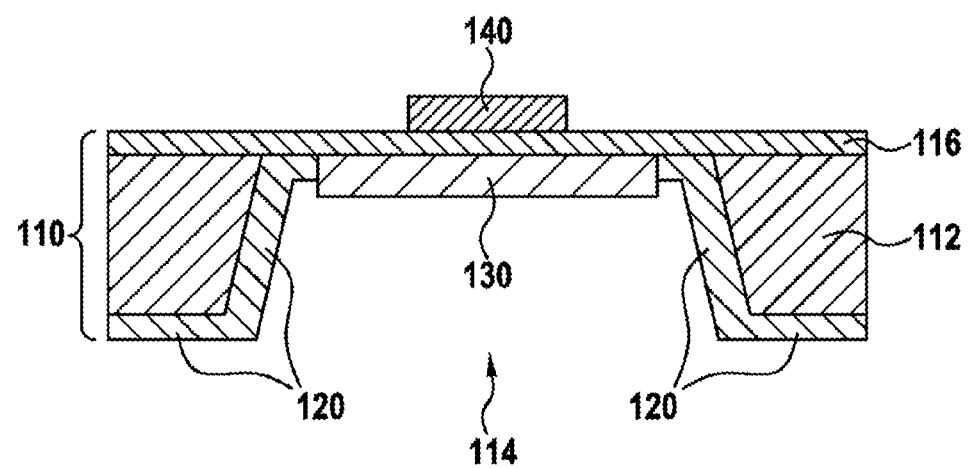

FIG. 2G shows a schematic sectional illustration of the gas sensor device 100 with produced or applied second measuring electrode 140 or front-side electrode. The gas sensor device 100 in FIG. 2G is thus shown in a state which corresponds to the state illustrated in FIG. 1. By way of example, the state of the gas sensor device 100 as shown in FIG. 2G is a produced or fabricated state.

FIGS. 2A to 2G show production states of the gas sensor device 100 or of the MECS sensor element during the progression of a production method using laser ablation in order to enable a use of functional electrodes applied wet-chemically for a rear-side contacting of the solid electrolyte layer 116 or of an electrolyte membrane. To put it another way, FIGS. 2A to 2G show an application of laser ablation for a method for producing the gas sensor device 100 with combined wet-chemical and dry-chemical deposition. This involves carrying out a selective laser ablation of the signal conductor layer 120, for example of a sputtered platinum layer, in the cutout section 222 from the adjoining solid electrolyte layer 116 in the cavity section 114, which has, in particular, a cavity having a depth of more than 200 micrometers.

Figure 3:
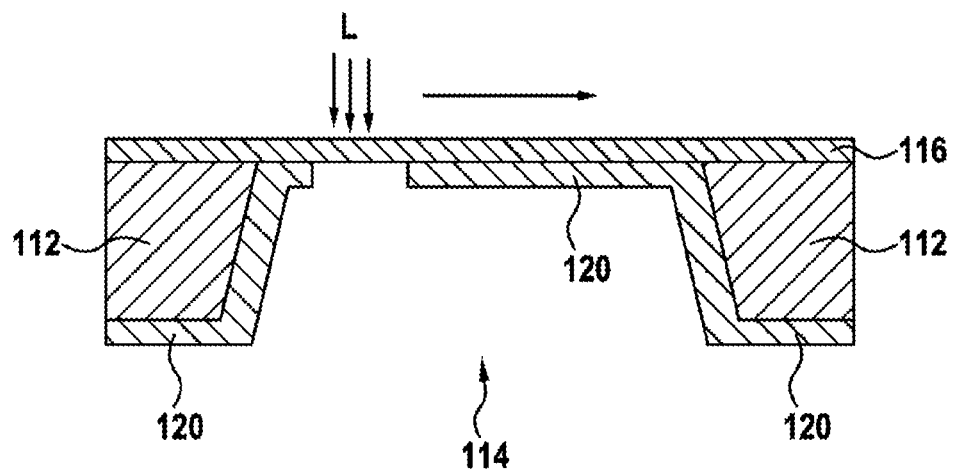

FIG. 3 shows a schematic sectional illustration of a sensor main body of a gas sensor device during the progression of a laser ablation in the context of a production method. The sensor main body is for example a sensor main body like the sensor main body from FIG. 2C, or the illustration in FIG. 3 corresponds to the illustration from FIG. 2C with the exception that the solid electrolyte layer 116 is shaped such that it is transparent to a laser L. Consequently, in FIG. 3, too, the partial section—adjoining the solid electrolyte layer 116—of the signal conductor layer 120 in the cavity section 114 is removed by laser ablation by means of the laser L. In this case, however, the laser L is arranged on the part of the solid electrolyte layer 116. A local laser ablation takes place in the cavity section 114 or at the bottom of the cavity. In FIG. 3, too, a direction of movement of the laser L is illustrated symbolically by an arrow. In this case, the laser ablation is carried out through the transparently embedded solid electrolyte layer 116 onto the partial section to be removed of the signal conductor layer 120.

In this case, the signal conductor layer 120 is deposited as layer to be ablated onto the solid electrolyte layer 116 embodied as an optically transparent membrane. A laser action on the part of the solid electrolyte layer 116 or from the wafer front side is thus possible in order to remove the signal conductor layer 120 deposited on the membrane rear side by means of the laser L. In this case, a maximum energy input of the laser L is effected at an interface between solid electrolyte layer 116 and signal conductor layer 120, wherein atomic layers directly adjoining the solid electrolyte layer 116 firstly evaporate. A clean layer removal from the solid electrolyte layer-signal conductor layer interface is thus effected. As a result, a required pulse energy of the laser L can be reduced, such that it is possible to realize both fast process times and ablation with little damage. For producing the laser L, pulsed beam sources can be used here, in particular having pulse lengths in the range of a few picoseconds and (a) short wavelength(s), for example frequency-doubled and -tripled YAG solid-state lasers (YAG=yttrium aluminum garnet).

FIGS. 4A to 4F show schematic sectional illustrations of at least partial sections of a gas sensor device in accordance with an exemplary embodiment of the present disclosure in different production states during the implementation of a variant of a production method. The gas sensor device is the gas sensor device from FIG. 1, for example.

Figure 4A:
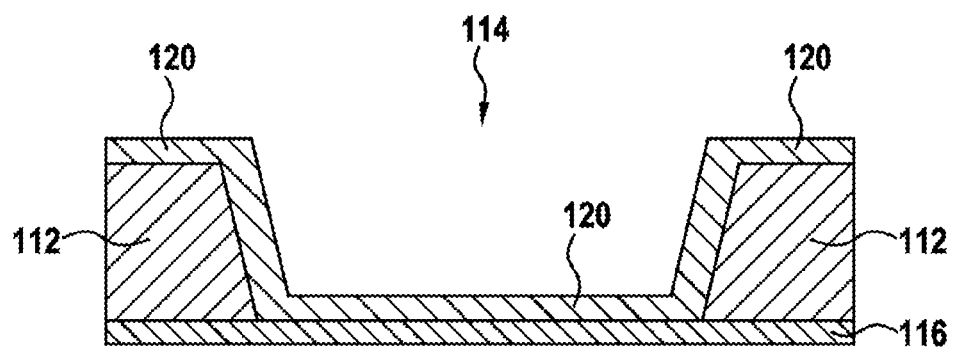

FIG. 4A shows a schematic sectional illustration of a sensor main body of the gas sensor device with a deposited signal conductor layer 120. Thus, in this case the sensor main body is shown in a production state in which the signal conductor layer 120 is produced by means of dry-chemical deposition, in particular by means of dry-chemical platinum coating, on the semiconductor substrate side of the sensor main body. In this case, the signal conductor layer 120 is deposited over the whole area on the semiconductor substrate side of the sensor main body.

Figure 4B:
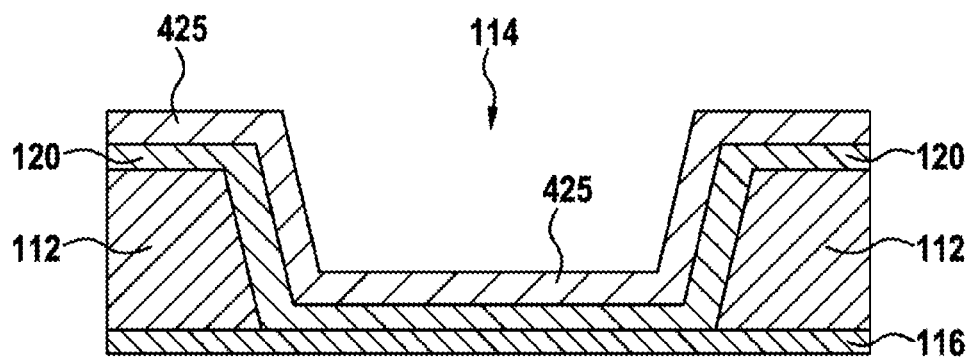

FIG. 4B shows a schematic sectional illustration of the sensor main body of the gas sensor device with a deposited signal conductor layer 120 from FIG. 4A with an additionally applied masking layer 425. In this case, a masking layer 425 is applied on the deposited signal conductor layer 120.

Figure 4C:
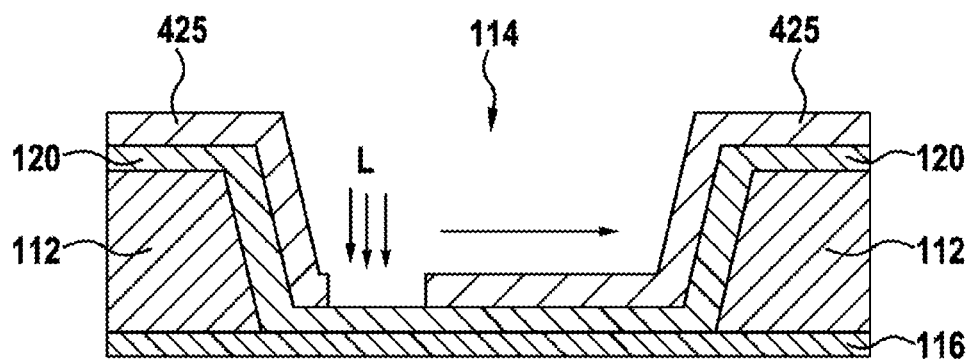

FIG. 4C shows a schematic sectional illustration of the sensor main body of the gas sensor device with a deposited signal conductor layer 120 and an applied masking layer 425 from FIG. 4B during the progression of a laser ablation. By means of a laser L, a partial section—adjoining the cutout section to be shaped in the signal conductor layer 120—of the masking layer 425 in the cavity section 114 is removed by laser ablation. In this case, the laser L is arranged on the part of the cavity section 114. FIG. 4C illustrates a direction of movement of the laser L symbolically by an arrow.

Figure 4D:
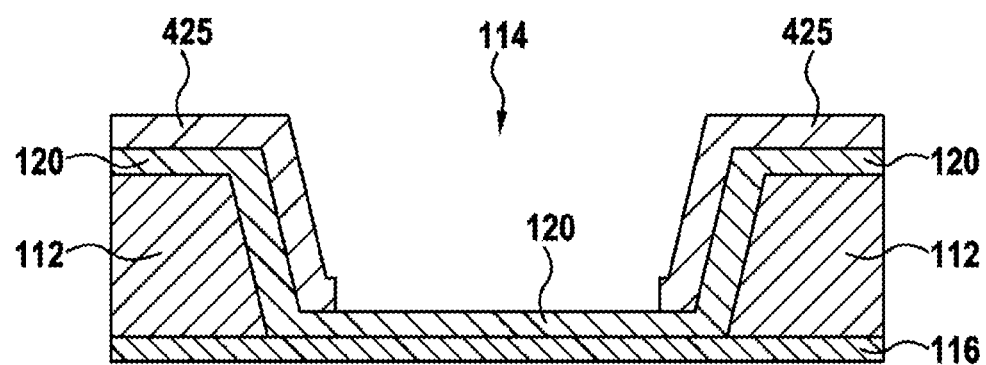

FIG. 4D shows a schematic sectional illustration of the sensor main body with the signal conductor layer 120 and the masking layer 425 from FIG. 4C after the laser ablation. In this case, the partial section—adjoining the cutout section—of the masking layer 425 in the cavity section 114 has been removed by laser ablation. A partial section of the signal conductor layer is thus exposed, in which partial section the cutout section is to be shaped. To put it another way, FIG. 4D shows the sensor main body from FIG. 4C after a selective laser ablation of a partial section of the masking layer 425.

Figure 4E:
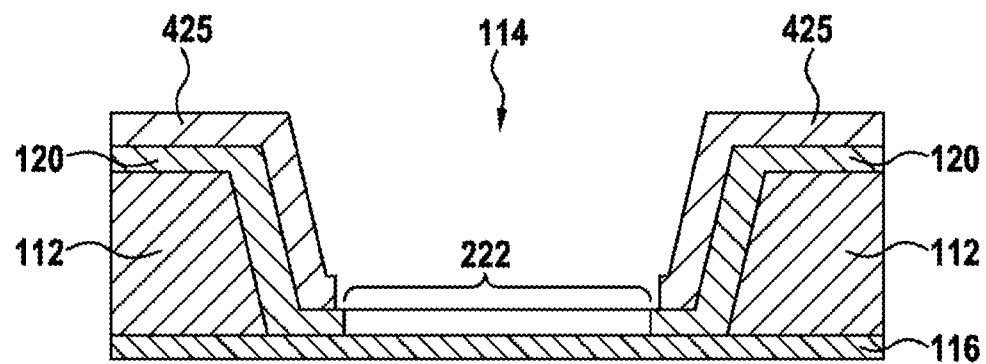

FIG. 4E shows a schematic sectional illustration of the sensor main body with the masking layer 425 partially removed by laser ablation from FIG. 4D after partial removal of the signal conductor layer 120 in a cutout section 222. In this case, in the cutout section 222, a partial section—adjoining the solid electrolyte layer 116—of the signal conductor layer 120 in the cavity section 114 has been removed for example by reactive ion etching or ion beam etching. The cutout section 222 mentioned in FIG. 1 has thus been produced in the signal conductor layer 120. A material of the signal conductor layer 120 has been removed in the cutout section 222. To put it another way, the signal conductor layer 120 is interrupted in the cutout section 222. The gas sensor device in FIG. 4E is thus shown in a partly fabricated state after structure transfer of the masking layer 425 to the signal conductor layer 120.

Figure 4F:
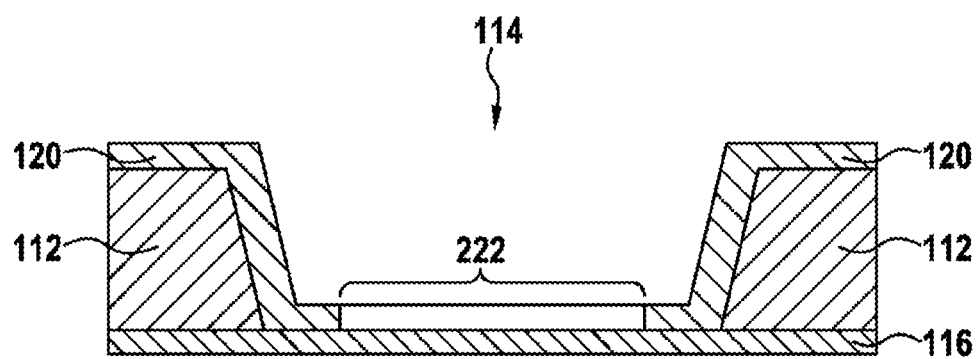

FIG. 4F shows a schematic sectional illustration of the partly fabricated gas sensor device from FIG. 2E after removal of the masking layer. FIG. 4F thus shows here, from the gas sensor device, the semiconductor substrate 112 with the cavity section 114, the solid electrolyte layer 116 and the signal conductor layer 120 with the cutout section 222. In this case, the masking layer has been removed in particular dry-chemically or wet-chemically.

To put it another way, FIGS. 4A to 4F illustrate an ablation using the masking layer 425. In the corresponding production methods, in this case, firstly the masking layer 425 is applied to the signal conductor layer 120 to be structured, as is evident from a comparative consideration of FIG. 4A and FIG. 4B, the masking layer 425 is then partially ablated, as is evident from FIG. 4C and FIG. 4D, and a structure of the masking layer 425 is then transferred into the signal conductor layer 120, as is evident from a comparative consideration of FIG. 4D and FIG. 4E. If necessary, the masking layer 425 is then removed, as is evident from a comparative consideration of FIG. 4E and FIG. 4F.

If direct ablation of the signal conductor layer 120 is not possible, there is thus the possibility of firstly applying a masking layer 425 to the signal conductor layer 120 by dry-chemical deposition and then ablating said masking layer 425. Afterward, the structure transfer to the signal conductor layer 120 is carried out and then, if necessary, removal of the masking layer 425. In this case, the masking layer 425 and the signal conductor layer 120 have a suitable difference in material parameters with regard to the selective ablation of the masking layer 425.

FIGS. 5A to 5F show schematic sectional illustrations of at least partial sections of a gas sensor device in accordance with an exemplary embodiment of the present disclosure in different production states during the implementation of a variant of a production method. The gas sensor device is the gas sensor device from FIG. 1, for example. The production method illustrated using FIGS. 5A to 5F is similar to the production method illustrated using FIGS. 2A to 2G.

Figure 5A:
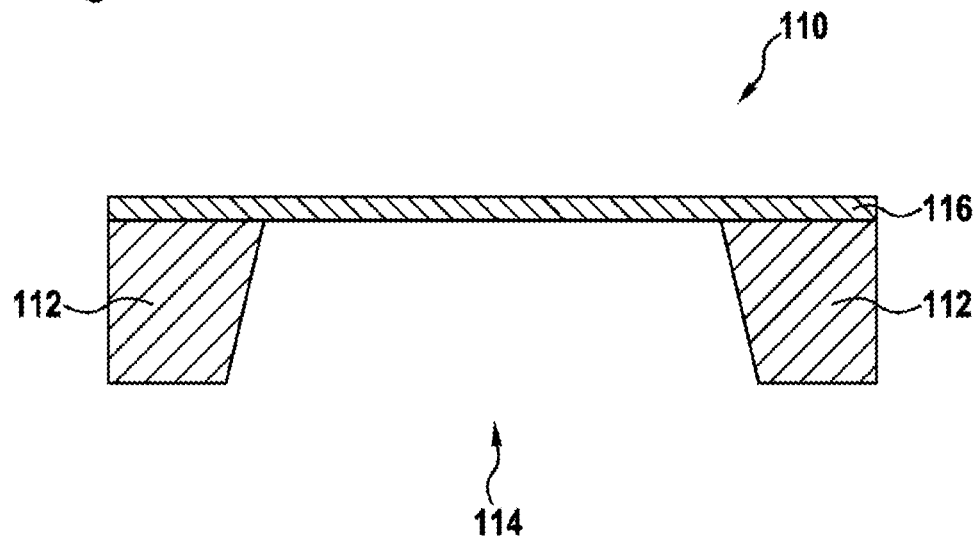

In this case, FIG. 5A shows a schematic sectional illustration of a sensor main body 110 of the gas sensor device. In this case, the sensor main body 110 is shown after a step of providing the sensor main body 110 in the production method. The sensor main body 110 comprises the semiconductor substrate 112 with the cavity section 114 and the solid electrolyte layer 116. The solid electrolyte layer 116 is embodied for example as a partially exposed or self-supporting yttrium-stabilized zirconium oxide electrolyte membrane or YSZ electrolyte membrane.

Figure 5B:
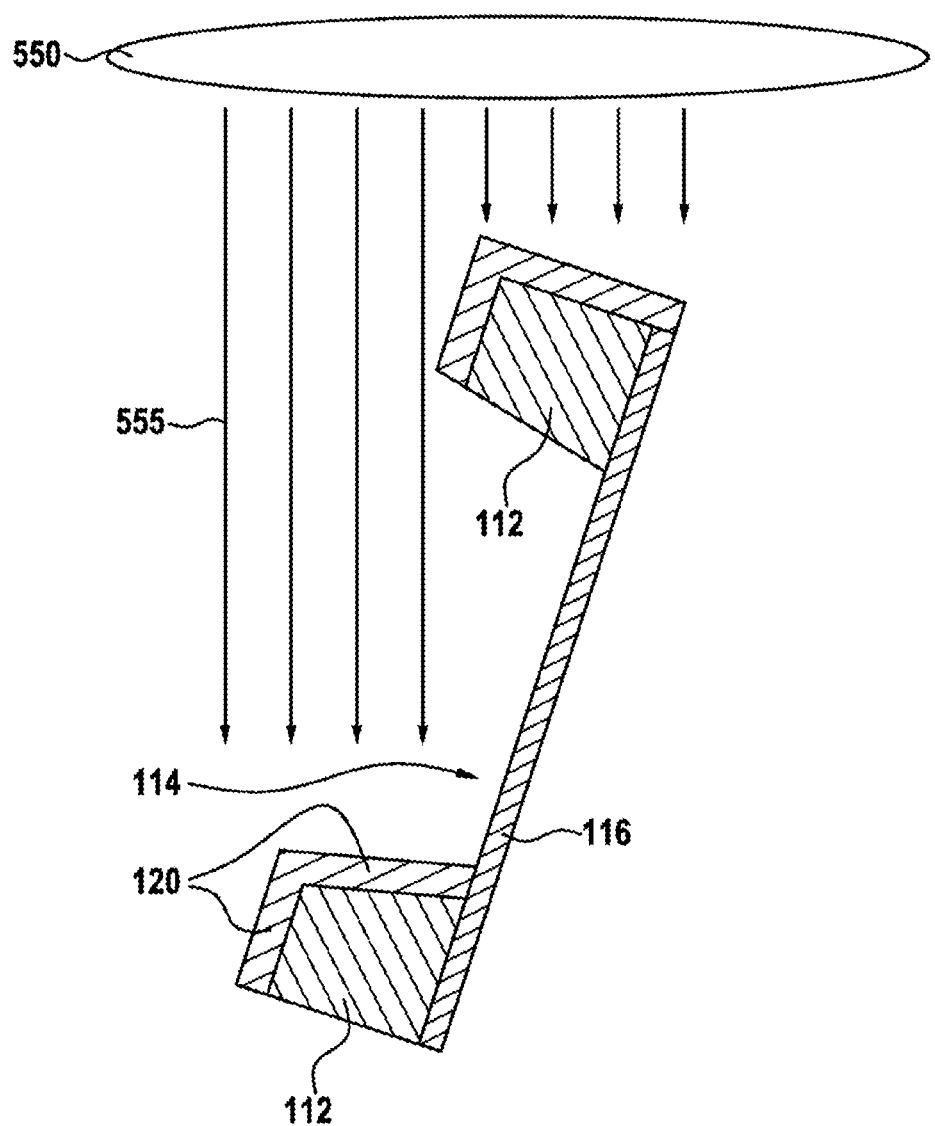

FIG. 5B shows a schematic sectional illustration of the sensor main body from FIG. 5A during the progression of a deposition of the signal conductor layer 120. In this case, the sensor main body is arranged adjacent to a material source 550, for example a so-called target, of a material of the signal conductor layer 120. In this case, a main extension plane of the solid electrolyte layer 116 or of the sensor main body is arranged transversely with respect to a deposition direction 555 of a deposition of the material of the signal conductor layer 120 from the material source 550. To put it another way, FIG. 5B illustrates, to be precise, a directional, dry-chemical platinum coating of the sensor main body with the signal conductor layer 120. In this case, the signal conductor layer 120 is deposited on partial sections of the semiconductor substrate 112. In this case, a section of the solid electrolyte layer 116 that is exposed in the cavity section 114 is shaded or geometrically shielded from the material of the signal conductor layer 120 that is deposited in the deposition direction 555. This geometrical shielding results from an orientation of the sensor main body in relation to the material source 550, the deposition direction 555 and geometrical properties of the cavity section 114.

Figure 5C:
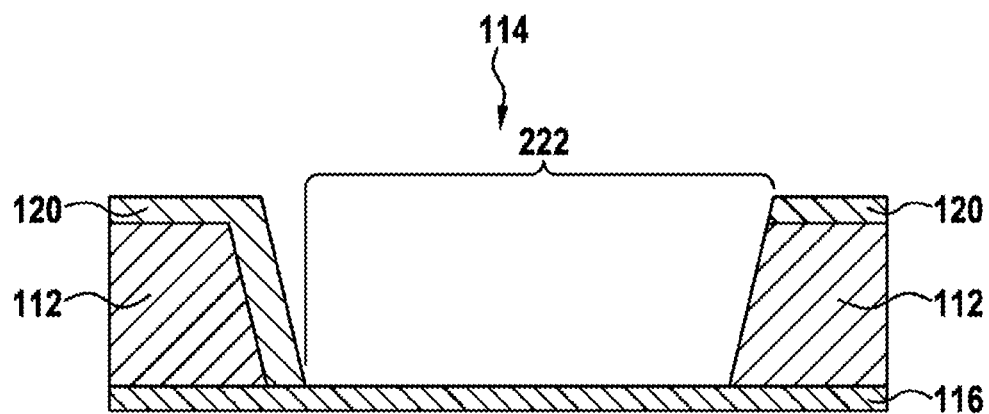

FIG. 5C shows a schematic sectional illustration of the sensor main body from FIG. 5B with a deposited signal conductor layer 120. The sensor main body is thus shown here in a production state in which the signal conductor layer 120 is produced by means of dry-chemical deposition, in particular by means of dry-chemical platinum coating, in partial sections of the semiconductor substrate 112, the majority on the semiconductor substrate side of the sensor main body. In this case, the signal conductor layer 120 is deposited in partial sections of the semiconductor substrate 112, the majority of which are arranged on the semiconductor substrate side of the sensor main body. To put it precisely, in this case the signal conductor layer 120 is deposited such that that section of the solid electrolyte layer 116 which is exposed in the cavity section 114 is free of the signal conductor layer 120. In particular, in this case in the sectional illustration by way of example only one sidewall of the cavity section 114 is covered with the signal conductor layer 120. A cutout section 222 is thus produced in the signal conductor layer 120, in which the signal conductor layer 120 is interrupted, cut out or not deposited. The cutout section 222 extends over that part of the solid electrolyte layer 116 which is exposed in the cavity section 114, and also by way of example over a sidewall of the cavity section 114 that is not covered by the material of the signal conductor layer 120. The cavity section 114 is thus embodied as a cavity with a sidewall platinum film. To put this another way, the gas sensor device in FIG. 5C is shown in a partly fabricated state.

Figure 5D:
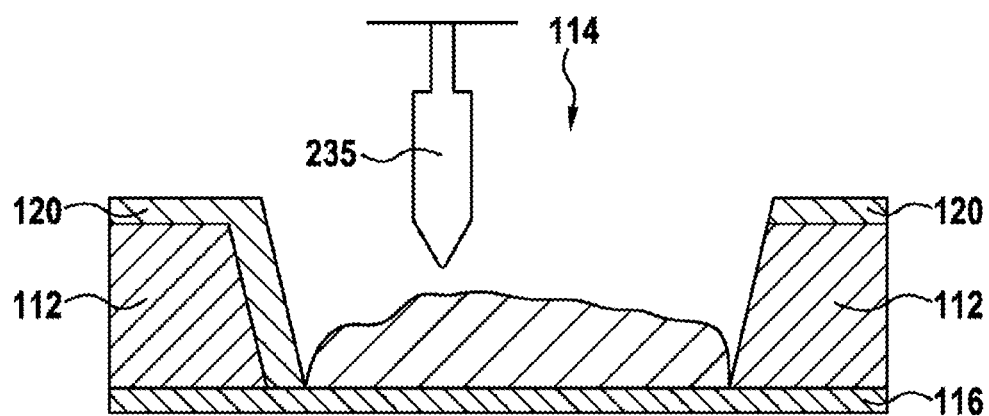

FIG. 5D shows a schematic sectional illustration of the partly fabricated gas sensor device from FIG. 5C with an applied electrode material 230 for a measuring electrode. In this case, the electrode material 230 is applied to the solid electrolyte layer 116 in the cutout section. To put it precisely, the electrode material 230 is applied to the solid electrolyte layer 116 wet-chemically in the cutout section of the signal conductor layer 120. The electrode material 230 is for example a platinum-containing material, in particular a platinum nanoparticle solution. The wet-chemical application of the electrode material 230 is carried out in this case for example by dispensing by means of an application tool 235.

Figure 5E:
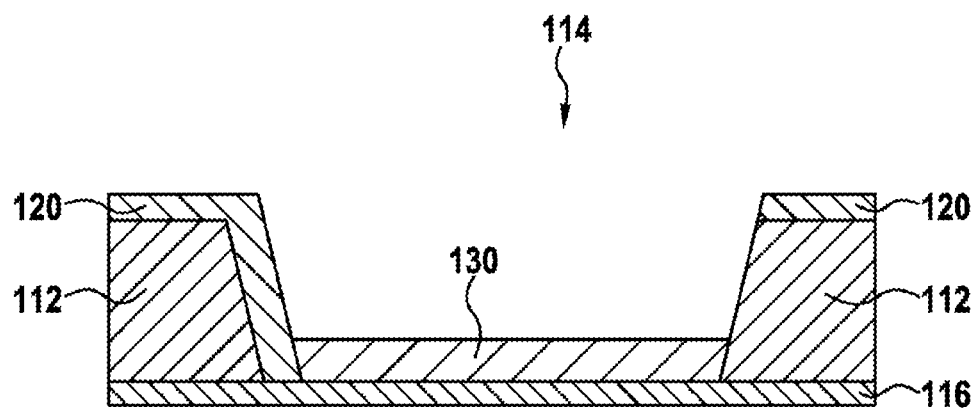

FIG. 5E shows a schematic sectional illustration of the partly fabricated gas sensor device from FIG. 5D with sintered electrode material or produced first measuring electrode 130. FIG. 5E thus illustrates the partly fabricated gas sensor device in a state in which the electrode material from FIG. 5D has been solidified by sintering and the first measuring electrode 130 has thus been produced. The first measuring electrode 130 is arranged on the solid electrolyte layer 116 in the cutout section of the signal conductor layer 120.

Figure 5F:
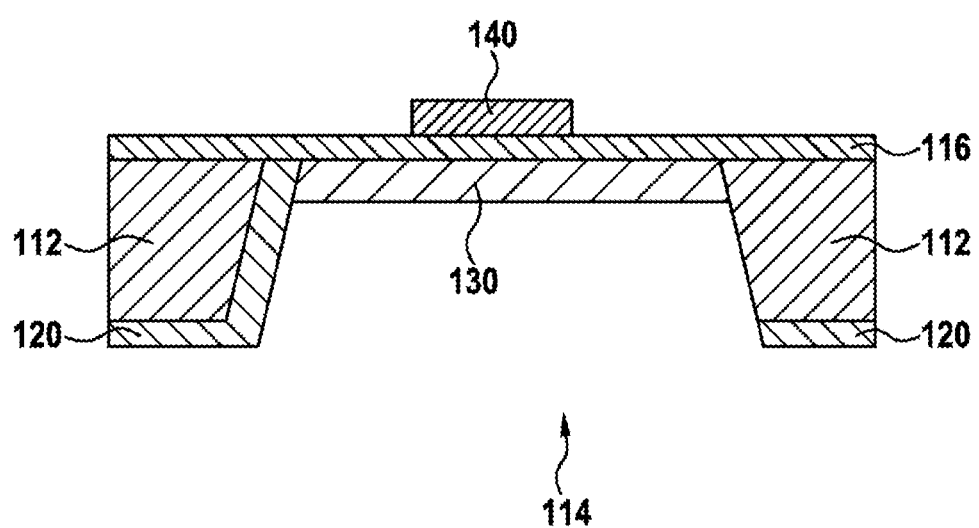

FIG. 5F shows a schematic sectional illustration of the gas sensor device 100 with produced or applied second measuring electrode 140 or front-side electrode. The gas sensor device 100 in FIG. 5F is thus shown in a state which corresponds to the state illustrated in FIG. 1, wherein the gas sensor device 100 is similar to that from FIG. 1. By way of example, the state of the gas sensor device 100 as shown in FIG. 5F is a produced or fabricated state.

To put it another way, FIGS. 5A to 5F show a use of a directional deposition method for a method for producing the gas sensor device 100 or an MECS sensor element in order to enable a use of functional electrodes supplied wet-chemically for a rear-side contacting of the solid electrolyte layer 116 or electrolyte membrane. A use of a combined deposition consisting of directional dry-chemical deposition and subsequent wet-chemical deposition is thus made possible. In this case, by way of example, the directional vacuum deposition of a compact metal film is effected, wherein the sensor main body 110 to be coated and the deposition direction 555 are oriented with respect to one another such that a deposition takes place substantially only on the sidewalls of the cavity section 114 and on a rear side of the semiconductor substrate 112. What are appropriate for directional depositions, inter alia, are preferably electron beam evaporation, with limitations also sputtering, ion beam assisted sputtering or similar methods. The angle between a main extension plane of the sensor main body 110 and the deposition direction 555, or how the same are oriented with respect to one another, depends here inter alia on a depth and/or a diameter of the cavity section 114. In this case, the solid electrolyte layer 116 exposed in the cavity section 114 or a bottom of the cavity remains largely uncoated in order that an access for a measuring gas comprising the at least one gaseous analyte to three-phase boundaries which are important for a microelectrochemical sensor and which are arranged between measuring gas, measuring electrodes 130 and 140 and the solid electrolyte layer 116 are not blocked for example by the signal conductor layer 120 or a compact platinum layer. After the deposition of the signal conductor layer 120 on the partial sections of the semiconductor substrate 112 or the cavity walls, the first measuring electrode 130 is deposited wet-chemically on the bottom of the cavity, wherein a layer thickness of an electrode film is chosen such that a contact to the signal conductor layer 120 on the cavity walls is produced.

Figure 6A:
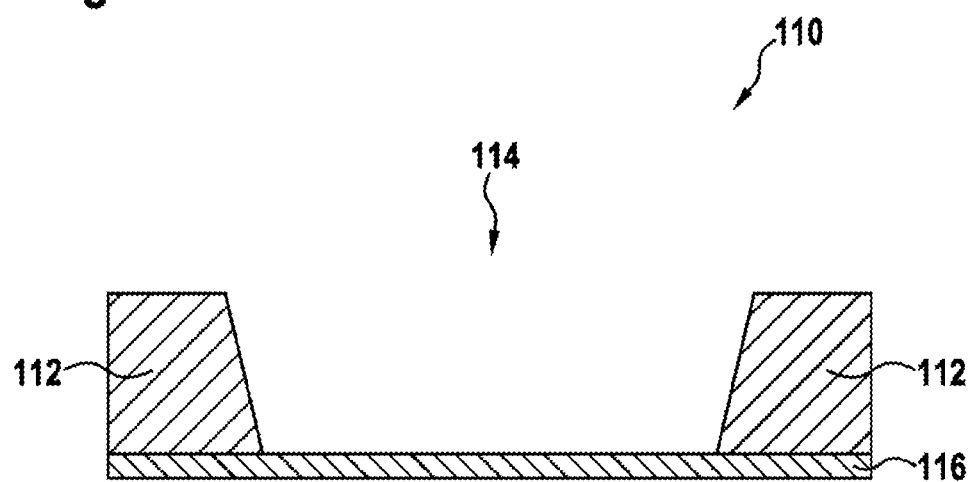
Figure 6B:
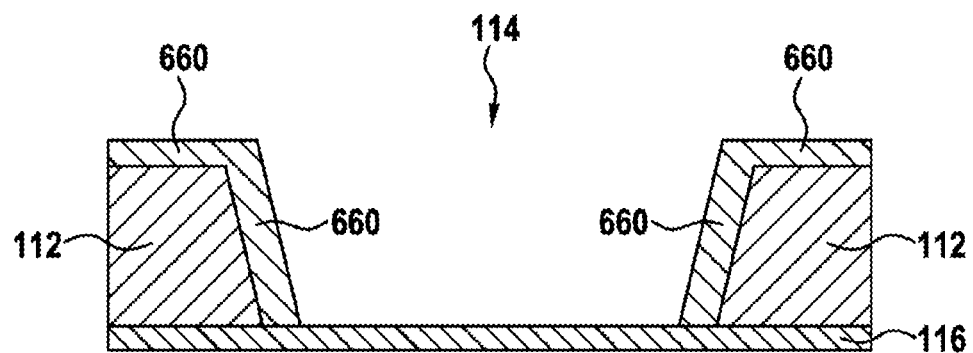

FIGS. 6A and 6B show schematic sectional illustrations of a sensor main body 110 of a gas sensor device in accordance with an exemplary embodiment of the present disclosure. In this case, the sensor main body 110 shown in FIG. 6A corresponds to one of the sensor main bodies from FIG. 2A and FIG. 5A. In FIG. 6B, the semiconductor substrate 112 on the semiconductor substrate side of the sensor main body is coated with a passivation layer 660. In particular any one of the sensor main bodies 110 of one of the gas sensor devices from FIG. 1, FIGS. 2A to 2G, FIG. 3, FIGS. 4A to 4F and FIGS. 5A to 5F can be coated with the passivation layer 660.

To put it another way, FIGS. 6A and 6B show a process of providing or arranging the passivation layer 660 on exposed surfaces of the semiconductor substrate 112 for protection against degradation of the substrate during operation of the gas sensor device for example in an exhaust gas. After coating with the passivation layer 660 or after a passivation, by way of example, a processing takes place in a manner similar or corresponding to the production method illustrated in FIGS. 5A to 5F, i.e. a directional metal deposition for producing a signal conductor layer and wet-chemical application of the measuring electrodes. Since a portion of the sidewalls of the cavity section 114 or of the cavity walls remains without being coated by the signal conductor layer, it may be necessary to provide these uncoated regions with the passivation layer 660 in order to avoid degradation of the silicon surface of the semiconductor substrate 112 during sensor operation, in particular during use in the exhaust gas of internal combustion engines. What are appropriate for the passivation layer 660 are for example oxide layers and nitride layers, such as, for example, silicon dioxide ($SiO_2$), silicon nitride (SiN), aluminum oxide (AlO), aluminum nitride (AlN), titanium oxide (TiO), titanium nitride (TiN) or the like. The passivation layer 660 can be provided by means of production methods customary in semiconductor technology, such as sputter deposition, chemical vapor deposition (CVD), atomic layer deposition, electron beam evaporation or pulsed laser deposition (PLD). A simple method for providing the passivation layer 660 exclusively on the unprotected silicon sidewalls of the semiconductor substrate 112 is a thermal oxidation of exposed silicon surfaces after a structuring or after a shaping of the cavity section 114.

Figure 7:
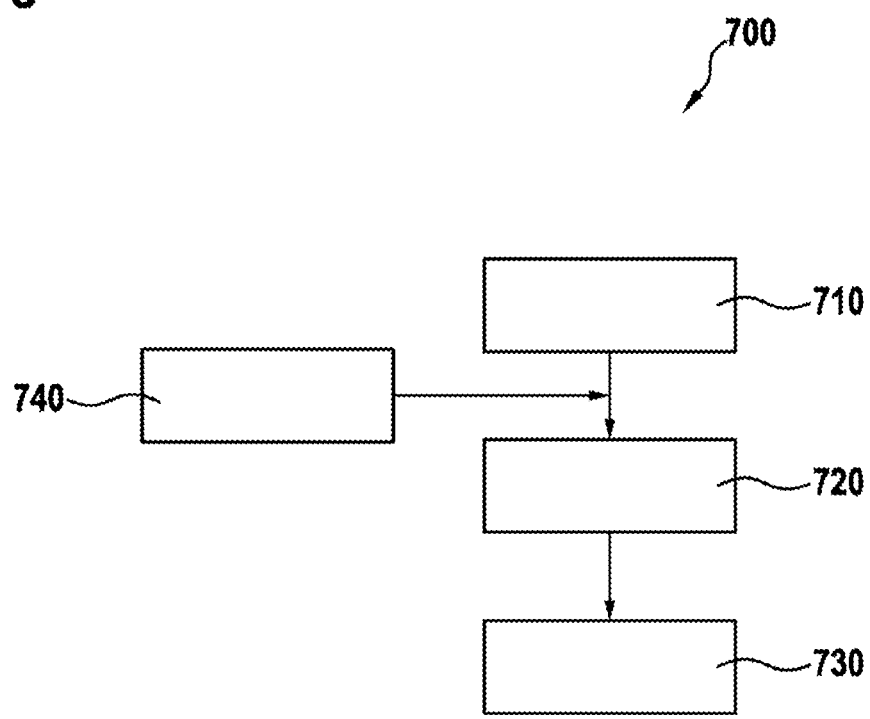
FIG. 7 shows a flow diagram of a method in accordance with one exemplary embodiment of the present disclosure.

FIG. 7 shows a flow diagram of a method 700 in accordance with one exemplary embodiment of the present disclosure. The method 700 is a method for producing a gas sensor device. In this case, the gas sensor device is designed to detect at least one gaseous analyte. The method 700 is thus implementable in order to produce a gas sensor device such as the gas sensor device from any of FIGS. 1 to 6B. To put it another way, a gas sensor device such as the gas sensor device from any of FIGS. 1 to 6B is producible by implementation of the method 700.

The method 700 comprises a step 710 of providing a sensor main body. In this case, the sensor main body comprises a semiconductor substrate, in which at least one cavity section is shaped, and a solid electrolyte layer arranged at a first main surface of the semiconductor substrate. In this case, the solid electrolyte layer in the at least one cavity section is not covered by, or is left free of, the semiconductor substrate.

In a step 720 of producing that can subsequently be carried out in the method 700, a signal conductor layer deposited dry-chemically is produced at a semiconductor substrate side of the sensor main body, such that, in the region of the solid electrolyte layer not covered by the semiconductor substrate in the at least one cavity section, at least one cutout section is shaped in the signal conductor layer, in which the signal conductor layer is removed or not deposited (or cut out).

In a step 730 of applying, following step 720 of producing, at least two measuring electrodes are applied to the solid electrolyte layer by means of a wet-chemical process. In this case, in step 730 of applying, a first measuring electrode is arranged in the at least one cutout section of the signal conductor layer. Furthermore, in this case, in step 730 of applying, a second measuring electrode is arranged on a solid electrolyte layer side of the sensor main body.

In accordance with one exemplary embodiment, in step 720 of producing, the signal conductor layer is deposited dry-chemically and is removed by means of selective laser ablation in the at least one cutout section. Alternatively, in step 720 of producing, the signal conductor layer is deposited dry-chemically in a defined deposition direction. In this case, depending on the deposition direction and a geometry of the at least one cavity section, the at least one cutout section is shaded from a material of the signal conductor layer. Optionally, in step 720 of producing, the signal conductor layer is deposited dry-chemically and is covered with a masking layer, the masking layer is then removed by means of selective laser ablation in the at least one cutout section, and the signal conductor layer is then removed in the at least one cutout section.

In accordance with one exemplary embodiment, the method 700 comprises a step 740 of coating the semiconductor substrate with a passivation layer. In this case, step 740 of coating is carried out before step 720 of producing the signal conductor layer.

The exemplary embodiments described and shown in the figures have been chosen merely by way of example. Different exemplary embodiments can be combined with one another completely or with regard to individual features. Moreover, an exemplary embodiment can be supplemented by features of a further exemplary embodiment.

Furthermore, the method steps presented here can be performed repeatedly and/or in a different order than that described.

If an exemplary embodiment comprises an "and/or" link between a first feature and a second feature, then this should be interpreted such that the exemplary embodiment has both the first feature and the second feature in accordance with one embodiment and either only the first feature or only the second feature in accordance with a further embodiment.

The invention claimed is:

1. A method for producing a gas sensor device for detecting at least one gaseous analyte, the method comprising:

providing a sensor main body comprising a semiconductor substrate, in which at least one cavity section is shaped, and a solid electrolyte layer arranged at a first main surface of the semiconductor substrate, wherein the solid electrolyte layer is left free of the semiconductor substrate in the at least one cavity section;

producing a signal conductor layer deposited dry-chemically at a semiconductor substrate side of the sensor main body, such that, in a region of the solid electrolyte layer not covered by the semiconductor substrate in the at least one cavity section, at least one cutout section is shaped in the signal conductor layer, in which the signal conductor layer is cut out; and applying at least two measuring electrodes to the solid electrolyte layer by a wet-chemical process, wherein a first measuring electrode is arranged in the at least one cutout section of the signal conductor layer and a second measuring electrode is arranged on a solid electrolyte layer side of the sensor main body.

2. The method as claimed in claim 1, wherein:
producing a signal conductor layer includes depositing the signal conductor layer dry-chemically and removing the signal conductor layer by selective laser ablation in the at least one cutout section.

3. The method as claimed in claim 2, wherein:
removing the signal conductor layer by selective laser ablation includes performing selective laser ablation from the semiconductor substrate side of the sensor main body and/or performing selective laser ablation from the solid electrolyte layer side of the sensor main body through the solid electrolyte layer, wherein the solid electrolyte layer is transparent to laser light used during the laser ablation.

4. The method as claimed in claim 1, wherein:
producing a signal conductor layer includes depositing the signal conductor layer dry-chemically in a defined deposition direction; and
depending on the deposition direction and a geometry of the at least one cavity section, the at least one cutout section is shaded from a material of the signal conductor layer.

5. The method as claimed in claim 1, wherein:
providing a sensor main body includes providing the sensor main body, in the semiconductor substrate of which the at least one cavity section is shaped with a depth of more than 100 micrometers.

6. The method as claimed in claim 1, further comprising:
coating the semiconductor substrate with a passivation layer, wherein coating the semiconductor substrate is carried out before producing the signal conductor layer.

7. The method as claimed in claim 1, wherein:
producing the signal conductor layer includes depositing the signal conductor layer dry-chemically and covering the signal conductor layer with a masking layer;
the masking layer is removed by selective laser ablation in the at least one cutout section; and
the signal conductor layer is removed in the at least one cutout section.

8. A device configured to carry out the method as claimed in claim 1.

9. The method as claimed in claim 1, wherein providing a sensor main body, producing a signal conductor layer, and applying at least two measuring electrodes are carried out via a computer processor executing a computer program stored on a non-transitory computer readable medium.

10. A gas sensor device for detecting at least one gaseous analyte, wherein the gas sensor device comprises:
a sensor main body, including:
a semiconductor substrate, in which at least one cavity section is shaped; and
a solid electrolyte layer arranged at a first main surface of the semiconductor substrate, wherein the solid electrolyte layer is left free of the semiconductor substrate in the at least one cavity section;
a signal conductor layer deposited dry-chemically at a semiconductor substrate side of the sensor main body, wherein in the region of the solid electrolyte layer not covered by the semiconductor substrate in the at least one cavity section, at least one cutout section is shaped in the signal conductor layer, in which the signal conductor layer is cut out; and
at least two measuring electrodes applied to the solid electrolyte layer by a wet-chemical process, wherein a first measuring electrode is arranged in the at least one cutout section of the signal conductor layer and a second measuring electrode is arranged on a solid electrolyte layer side of the sensor main body.

* * * * *